(12) United States Patent
Fogel

(10) Patent No.: US 9,393,143 B1
(45) Date of Patent: Jul. 19, 2016

(54) ENDOSCOPIC IMPLANTABLE CLAMP-LIKE DEVICE FOR THE APPOSITION OF THE STOMACH WALLS FOR REDUCING THE STOMACH INTERNAL VOLUME IN A WEIGHT LOSS SURGERY PROCEDURE

(71) Applicant: Roberto Fogel, Sunny Isles Beach, FL (US)

(72) Inventor: Roberto Fogel, Sunny Isles Beach, FL (US)

( * ) Notice: Subject to any disclaimer, the term of this patent is extended or adjusted under 35 U.S.C. 154(b) by 289 days.

(21) Appl. No.: 14/299,277

(22) Filed: Jun. 9, 2014

Related U.S. Application Data

(63) Continuation of application No. 13/277,374, filed on Oct. 20, 2011, now abandoned.

(60) Provisional application No. 61/405,667, filed on Oct. 22, 2010.

(51) Int. Cl.
*A61F 2/04* (2013.01)
*A61F 5/00* (2006.01)

(52) U.S. Cl.
CPC .................................. *A61F 5/0086* (2013.01)

(58) Field of Classification Search
CPC ... A61F 5/0086; A61B 17/122; A61B 17/072
See application file for complete search history.

(56) References Cited

U.S. PATENT DOCUMENTS

| | | | |
|---|---|---|---|
| 2004/0138526 A1* | 7/2004 | Guenst | A61B 17/0218 600/114 |
| 2004/0193190 A1* | 9/2004 | Liddicoat | A61B 17/00234 606/153 |

* cited by examiner

*Primary Examiner* — Richard Louis

(57) ABSTRACT

An implantable endoscopic apparatus for apposition to a wall of a stomach has an elongated endoscopic tube, a vacuum pump connected to the tube, a body releasably affixed to the distal end of the tube, and an actuator cooperative with the body so as to open and close the body. The body has suction nozzles formed on a wall of the body and has grabbing teeth formed along edge of the body. The halves of the body can open so as to expose the suction nozzles to the stomach wall. The halves of the body can close such that the grabbing teeth grasp the stomach wall so as to reduce stomach volume.

7 Claims, 4 Drawing Sheets

ENDOSCOPIC IMPLANTABLE CLAMP-LIKE DEVICE FOR THE APPOSITION OF THE STOMACH WALLS FOR REDUCING THE STOMACH INTERNAL VOLUME IN A WEIGHT LOSS SURGERY PROCEDURE

CROSS-REFERENCE TO RELATED APPLICATIONS

This Continuation-In-Part Application claims the benefit of co-pending U.S. Non-Provisional patent application Ser. No. 13/277,374, filed on Oct. 20, 2011, which in turn claims the benefit of U.S. Provisional Patent Application Ser. No. 61/405,667, filed on Oct. 22, 2010, all of which are incorporated herein in their entirety.

BACKGROUND OF THE INVENTION

1. Field of the Invention

This invention relates generally to an endoscopic implantable device and method capable of delivering, during a weight loss surgery procedure, a functional device through the patient's esophagus and to the stomach where it is attached to the stomach walls. More particularly, the present invention is referred to an endoscopic implantable device for the apposition of the stomach walls by delivering the device to the stomach, opening it up, creating a suction effect for attracting the stomach walls, closing it and leaving the device into the stomach reducing the internal volume of the stomach. Even more particularly, the present invention is referred to a method for the apposition of different types of tissue, including but not limited to, the stomach walls, fistulas, hemorrhages, etc.

2. Description of the Prior Art

Obesity is a medical condition in which excess body fat has accumulated to the extent that it may have an adverse effect on health, leading to reduced life expectancy. Body mass index (BMI), which compares weight and height, is used to define a person as overweight when their BMI is between 25 kg/m$^2$ and 30 kg/m$^2$ and obese when it is greater than 30 kg/m$^2$.

Obesity is associated with many diseases, particularly heart disease, type 2 diabetes, breathing difficulties during sleep, certain types of cancer, and osteoarthritis. Obesity is most commonly caused by a combination of excessive dietary calories, lack of physical activity, and genetic susceptibility, though a limited number of cases are due solely to genetics, medical reasons or psychiatric illness.

Obesity is a leading preventable cause of death worldwide, with increasing prevalence in adults and children, and authorities view it as one of the most serious public health problems of the 21st century. Annual medical expenditures attributable to obesity have doubled in less than a decade, and may be as high as $147 billion per year, according to a new study by researchers at RTI International, the Agency for Healthcare Research and Quality, and the U.S. Centers for Disease Control & Prevention.

The study, published on the Health Affairs' website, reports that, between 1998 and 2006, the prevalence of obesity (body mass index greater than 30) increased by 37 percent. This increase is responsible for 89 percent of the increase in obesity costs that occurred during this time period. The results reveal that obesity is now responsible for 9.1 percent of annual medical expenditures, compared with 6.5 percent in 1998. The medical costs attributable to obesity are almost entirely a result of costs generated from treating the diseases that obesity promotes.

There have been several approaches to treat obesity. The primary treatment for obesity is dieting and physical exercise. If this fails, anti-obesity drugs may be taken to reduce appetite or inhibit fat absorption. In severe cases, there are different surgery possibilities. Bariatric surgery, or weight loss surgery, is performed on the stomach and intestine of people who are dangerously obese, for the purpose of losing weight. The two most common procedures are the Roux-en-Y, which closes off a portion of the stomach and bypasses part of the intestine; and gastric banding, which places a band around the stomach. In long-term studies, the procedures caused a significant long-term loss of weight, recovery from diabetes, improvement in cardiovascular risk factors, and a reduction in mortality of 23% to 40%.

Another option is the laparoscopic bariatric surgery that requires a hospital stay of 1-2 days. Short-term complications from laparoscopic adjustable gastric banding are lower than laparoscopic Roux-en-Y surgery, and complications from laparoscopic Roux-en-Y surgery are lower than open Roux-en-Y surgery, although gastric banding and Roux-en-Y do not have the same long term effects, according to a July 2009 study of experienced centers. Overall, 30-day mortality from the surgery itself was 0.3% and the rate of major complications was 4.3%. Gastric banding had no deaths and 4.8% major complications; laparoscopic Roux-en-Y had 0.2% surgical deaths and 1.0% major complications, and open Roux-en-Y had 2.1% surgical deaths and 7.8% major complications, in 4,776 patients with an average body mass index (BMI) of 46.5. Complications were higher in patients with higher BMIs and obstructive sleep apnea.

The National Institutes of Health recommends bariatric surgery for obese people with a BMI of at least 40, and for people with BMI 35 and serious coexisting medical conditions such as diabetes.

There are several bariatric procedures known in the art. For example, US Patent Application Serial Number 2006/0047289 of the inventor of the present invention teaches about a bariatric procedure named endoscopic tissue apposition device that includes a vacuum chamber configured to securely hold a portion of tissue therein, the vacuum chamber being defined by a proximal wall and a distal wall opposite to the proximal wall. Working and vacuum channels are provided in communication with the vacuum chamber. A portion of tissue is held in the vacuum chamber when the vacuum is applied in the vacuum chamber through the vacuum channel A carrier needle is disposed on a proximal side of the vacuum chamber and is longitudinally advanceable into and across the vacuum chamber, while a punch needle is disposed on a distal side of the vacuum chamber and is configured to receive the carrier needle therein. A hold and release mechanism holds and releases the punch needle to facilitate joining portions of tissue together.

Also the USSN 2003/0208209 of Richard A. Gambale et al. discloses an improved endoscopic tissue apposition device having multiple suction ports that permits multiple folds of tissue to be captured in the suction ports with a single positioning of the device and attached together by a tissue securement mechanism such as a suture, staple or other form of tissue bonding. The improvement reduces the number of intubations required during an endoscopic procedure to suture tissue or join areas of tissue together. The suction ports may be arranged in a variety of configurations on the apposition device to best suit the desired resulting tissue orientation. The tissue apposition device may also incorporate a tissue abrasion means to activate the healing process on surfaces of tissue areas that are to be joined by the operation of the device to promote a more secure attachment by permanent tissue bonding.

U.S. Pat. No. 6,773,440 of Gannoe et al. describes a device for use in acquiring tissue folds from the anterior and posterior portions of a hollow body organ, e.g., a stomach, positioning the tissue folds for affixing within a fixation zone of the stomach, preferably to create a pouch or partition below the esophagus, and fastening the tissue folds such that a tissue bridge forms excluding the pouch from the greater stomach cavity. It also includes a transoral, endoscopic hollow organ division, including a tissue acquisition device capable of acquiring the desired tissue, a tensioning device for positioning the acquired tissue, and a fastening element to secure the outer layers of the acquired tissue such that the desired healing response is achieved.

U.S. Pat. No. 7,122,058 of Levine et al. describes an apparatus for limiting absorption of food products in specific parts of the digestive system. A gastrointestinal implant device is anchored in the stomach and extends beyond the ligament of Treitz. All food exiting the stomach is funneled through the device. The gastrointestinal device includes an anchor for anchoring the device to the stomach and a flexible sleeve to limit absorption of nutrients in the duodenum. The anchor is collapsible for endoscopic delivery and removal.

U.S. Pat. No. 7,172,613 of Wazne describes an intragastric device inserted by endoscopic path into a patient's stomach. The device includes a balloon or envelope having a specific nominal volume. The balloon is sealingly connected to connecting elements consisting of a disc forming a support base for the balloon against an inner wall of the stomach. The device also includes a flexible tube or catheter for connecting the balloon to a filling device and catching element integral with the tube or catheter. The connection elements enable a doctor to set and/or remove the balloon and to fix, either inside the patient's body, or subcutaneously the filling device and to be able to bring the balloon or envelope to its predetermined nominal volume.

United States Patent Application Serial Nr. 20070260278 of Wheeler; William K. et al. describes a an apparatus, systems, and methods for closing the base of a left atrial appendage or other tissue structure. A tissue closure device comprises a pair of legs having compliant surfaces for engaging against opposite sides of the tissue structure. A plurality of axially spaced-apart tissue-penetrating fasteners are delivered from one leg to the other to pierce the intervening tissue and hold the closure device in place on the tissue structure. This patent fails completely in describing an apparatus capable of reducing the volume of a stomach. It does not describe a clamp-like structure capable of being left into the stomach during an endoscopic procedure. This is a stapler-like device. The stapler is inserted into the patient's body. Once the spot to be treated is located, the stapler is fired and a fastener is attached to the organ. The suction device is used to open and close the device and not to attract the walls of the stomach. The device is not recoverable in the Weller patent. In the present invention, the suction is strong enough to attract the walls of the stomach. Also, the outer edges of the body have grabbing teeth that are used to keep the device in place and the volume of the stomach reduced. The Weller patent is not disclose teeth in the nature of the present invention. The Weller patent does not teach the use of any suction from the inner walls of the body so as to attract the stomach wall. As such, the Weller patent fails to show or suggest the present invention.

United States Patent Application Serial Number 20050203547 of Weller, Gary; et al. describes devices and methods for tissue acquisition and fixation, or gastroplasty These devices may be advanced in a minimally invasive manner within a patient's body, e.g., transorally, endoscopically, percutaneously, etc., to create one or several divisions within the hollow body organ. Such divisions can form restrictive barriers within a organ, or can be placed to form a pouch, or gastric lumen, smaller than the remaining stomach volume to essentially act as the active stomach such as the pouch resulting from a surgical Roux-En-Y gastric bypass procedure. Moreover, the system is configured such that once acquisition of the tissue by the gastroplasty device is accomplished, any manipulation of the acquired tissue is unnecessary as the device is able to automatically configure the acquired tissue into a desired configuration. This patent fails to describe a clamp-like device with two complementary halves, each of which including teeth for grabbing and keeping the stomach tissue together.

United States Patent Application Serial Nr. 20070213747 of Monassevitch; Leonid; et al. discloses a surgical clip assembly which includes a pair of generally linear compression elements for securing tissue between them and for applying to the secured tissue a compression force. The clip assembly has an initial, open position in which the linear compression elements may be positioned about tissue to be secured between them. The assembly also has a final, closed position where the compression elements are substantially parallel to each other, applying a compressive force to the secured tissue. The clip assembly also includes a force means disposed between the pair of compression elements and operative to transmit operational forces between them. As in the previous cases, this patent fails to describe the combination of a clamp-like device, with two complementary halves with suction means, and a set of two opposing set of teeth. This device includes two sets of teeth but they are parallel to each other. It fails to relate them to a bariatric procedure for reducing the volume of a stomach. It is not possible to reduce the volume of a stomach using this device, as it is designed for joining tissue portions at the site of organ resections Importantly, the prior art combination would fail to show the features of the present invention as defined by independent claim 1 herein. In particular, the prior art combination fails to show the first wall and the second wall defining an "internal chamber" in the device. The prior art combination fails to show a plurality of suction nozzles that are formed on the "first wall". The prior art combination fails to show the grabbing teeth that extend along an edge "opposite" the hinged connection between the halves of the body. Additionally, and furthermore, the prior art combination would fail to show the "grabbing teeth" that are formed along this edge such that they intermesh with each other when the body is closed.

Even though all the above mentioned methods and devices represent a partial solution, they are very invasive and sometimes the patient needs to be hospitalized for a couple of days. The risks are higher than recommended or the costs and time involved for the procedure are extremely high.

As such, an endoscopic implantable device and method for the apposition of the stomach walls for reducing the stomach internal volume is still desired in the market.

SUMMARY OF THE INVENTION

A main object of the present invention is to provide an implantable device for reducing the stomach volume without having to stitch the stomach walls, using a procedure that only takes several minutes with no risk to the patient's life.

Another object of the present invention is to provide a method for reducing the stomach volume by introducing a device which grabs the stomach walls and keeps them united for a period of time the surgeon considers appropriate to reduce the patient's weight. After said time, the device may be taken out during an additional reversing procedure or may be absorbed by the gastric fluids with no side effects for the patient.

Yet another object of the present invention is to provide an endoscopic apposition device that is simple and economical to produce and use.

According to another aspect of the invention, a tissue apposition device is provided having longitudinal flexibility that is easily navigable through a natural body lumen while mounted at the distal end of an elongated tube.

Yet another aspect of the invention provides a device for joining stomach tissue that captures at least two areas of tissue at the same time by suction action and closing the implant device to join them together.

Yet another aspect of the invention provides a device for reducing the internal volume of an overweight patient, especially useful for patients that are 60-80 lbs overweight.

Yet another aspect of the invention provides a device for closing a bleeding fistula and/or a hemorrhage by placing a biodegradable device on the critical place to close the injury.

In summary, the present invention is referred to an endoscopic implantable device for the apposition of the stomach walls for reducing the stomach internal volume, comprising an elongated endoscopic flexible tube having a proximal end and a distal end, said endoscopic tube having a vacuum channel formed therein; a vacuum pump connected to said endoscopic tube so as to create a vacuum through said vacuum channel so as to create a vacuum at said distal end of said endoscopic tube; a body releasably affixed to said distal end of said flexible tube, said body having a first half hingedly connected to a second half, each of said first and second halves having a first wall in spaced relation to a second wall so as to define an internal chamber in fluid communication with said vacuum channel of said endoscopic tube, said first wall having a plurality of suction nozzles in fluid communication with said internal chamber, said first half of said body having a first set of grabbing teeth formed along an edge thereof opposite the hinged connection with said second half, said second half having a second set of grabbing teeth formed along an edge thereof opposite the hinged connection with said first half; and an actuator cooperative with said body so as to move said first and second halves between an open position and a closed position, said edges and said grabbing teeth of said first and second halves being spaced from each other in said open position, said edges of said first and second halves being adjacent each other in said closed position such that said first set of grabbing teeth intermesh with said second set of grabbing teeth.

These and other aspects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

DETAILED DESCRIPTION OF REPRESENTATIVE EMBODIMENTS

Figure 1:
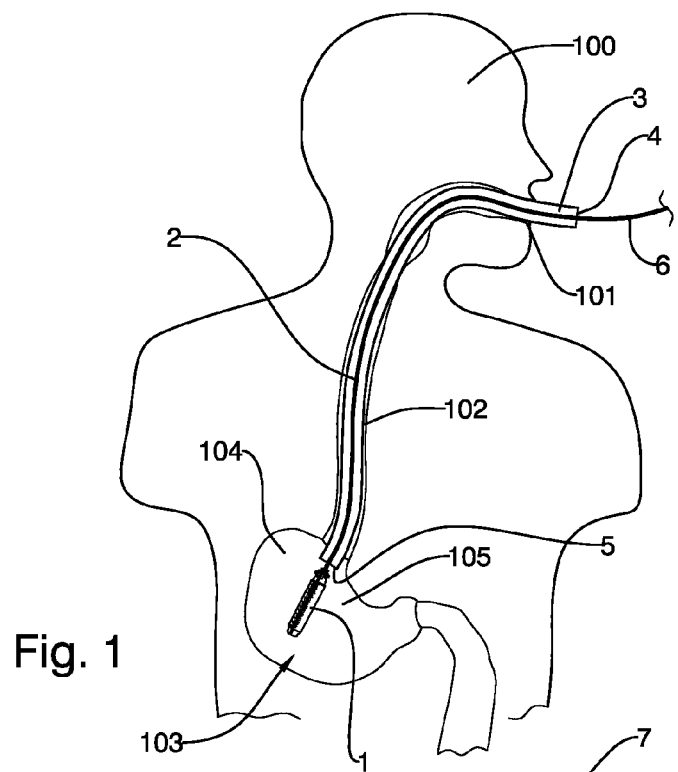
FIG. 1 illustrates a general schematic view of a patient and illustrates how the elongated tube enters the esophagus and into the stomach with the purposed device inserted in the distal end thereof.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices illustrated in the attached drawings, and described in the following specification, are simply exemplary embodiments of the inventive concepts defined in the appended claim. Hence, specific dimensions and other physical characteristics relating to the embodiments disclosed herein are not to be considered as limiting, unless the claims expressly state otherwise.

The present invention provides an endoscopic implantable device for the apposition of the stomach walls for reducing the stomach internal volume, capable of securing a tissue site together with a single intubation of an elongated tube carrying the device at the distal end thereof into the stomach of the patient. To position the suture in the appropriate locations, the purposed device may be releasably secured to the distal end of any suitable elongated tube. The device also includes a tissue vacuum chamber that creates a suction effect and captures a section of stomach tissue therein, closing the device and capturing a portion thereof with a set of teeth.

Shown throughout the Figures, the invention is directed to an endoscopic device 1 for reducing the internal volume of the patient's stomach. To introduce this device 1 into the stomach, an elongated flexible tube 2 is used, comprising an elongated flexible body 3 with an upper end 4 and a distal end 5. Inside said tube 3, an operating device 6 is included which provides two basic functions: opening-closing the device and providing a suction means as will be explained in detail below.

The above mentioned distal end 5 includes an operating head 7, including retention means 8 and two operating arms 9-10. Said retention means 8 maintains the purposed device 1 attached to the elongated tube 2, and the arms 9-10 open and close the device halves.

Figure 3:
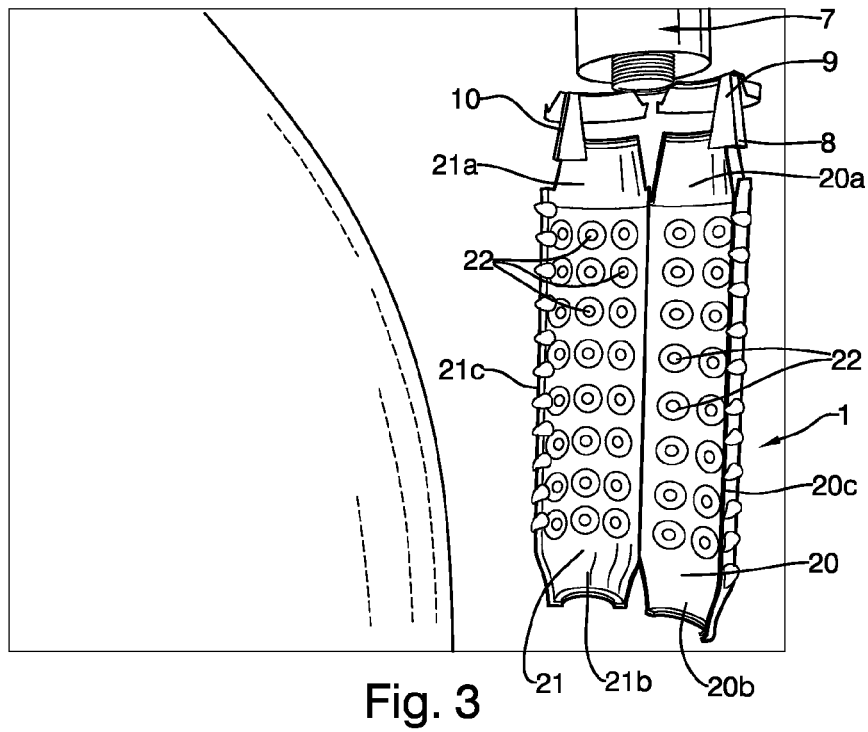
FIG. 3 is a perspective view of the purposed device in an open position, showing in detail the two hinged halves that define the same, the suction nozzles and the mechanism that opens said halves. In this case the device in open but the suction nozzles are not suctioning yet. It is in a passive position.

The device comprises a cylindrical clamp-like body defined by two halves 20-21 each of which includes an upper end 20a-21a and a distal end 20b-21b. On the inner surface of each half 20-21, a plurality of suction nozzles 22 are included. Each nozzle is in fluid communication with a suction means of the elongated tube 2. Also a regular endoscope (not illustrated) may also be used to give to the surgeon a visual indication of the site in which the device will be placed. As illustrated in FIG. 3, said nozzles 22 are evenly distributed on the inner surface of each half 20-21. This is to create an even suction effect on the stomach wall.

On the external side 20c-21c of each half 20-21 an aligned plurality of teeth 24 are included. The teeth 24 of half 20 are slightly offset regarding teeth 24 of half 21 so as to create an interlocking effect when the device is in the closed position illustrated in FIG. 2.

FIG. 1 shows how the elongated tube with the purposed device is inserted into the patient's body. As shown, it is not necessary to make any incision in the skin and the stomach as in the laparoscopic surgeries. The purposed system comprises a flexible endoscopic device 1 designed to be inserted through the mouth into the stomach. The procedure is performed under general anesthesia and takes roughly half an hour to complete. Per the standard safety protocol, the patient is placed on a respirator to help regulate his/her breathing during the surgery. Once the patient 100 has been sedated and is breathing comfortably, the endoscopic device 1 is inserted into the mouth 101 and fed through the esophagus 102 to the stomach 103. The bariatric surgeon will then insert the operative commands 6 for controlling the device, including a regular endoscope with a flexible camera to be able to see during the procedure (not illustrated), the suction conduit which provides the necessary suction effect to the suction nozzles, and the opening-closing means. The device 1 is located inside the stomach somewhere between the fundus 104 and the middle body 105 of the stomach 103.

Figure 2:
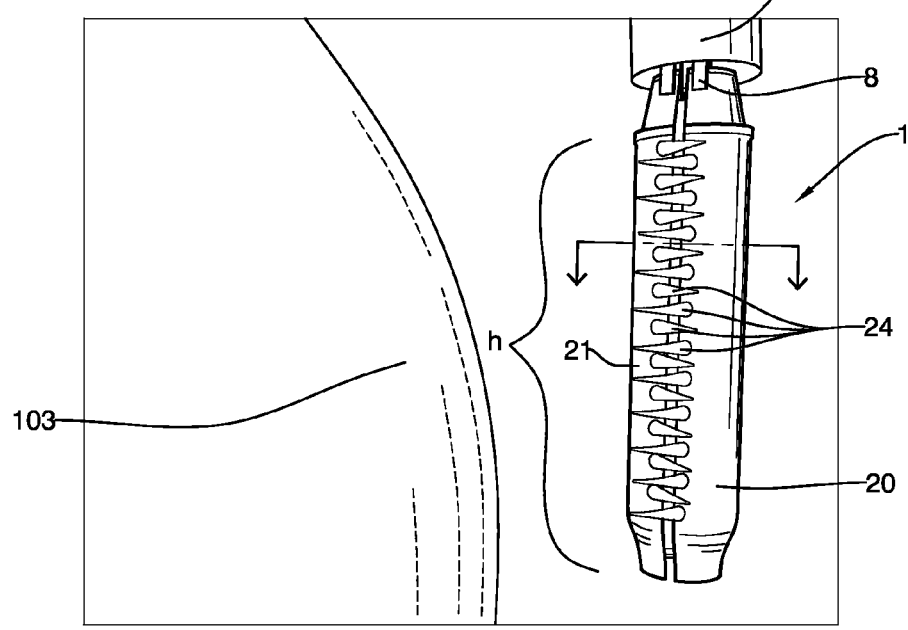
FIG. 2 is a perspective view of the purposed device, attached to the distal end of the elongated tube in its closed position. In this figure the device is already placed into the stomach, between the middle stomach and fundus.

FIG. 2 illustrates the purposed device 1 in the stomach 103. The device is closed so teeth 24 surround the external wall of the device in an intermeshing pattern. Both halves 20-21 in this closed position form a cylindrical piece and the length 'h' will depend on the patient's size. It is obvious that those patients who have a larger body will need a longer (and consequently larger suction surface) device.

FIG. 3 illustrates the purposed device in its open position. In order to be able to open it, the surgeon must operate on the controlling means 6. By turning a controlling wheel (not illustrated) at the upper end of the elongated tube, the surgeon will produce the rotation of arms 9-10 and consequently the separation of halves 20-21 and thus the opening of device 1. When the device is open, the inner surface of said halves 20-21 are exposed to the internal wall of the stomach. The distribution of the suction nozzles 22 in each half 20-21 will create an even suction effect. Nevertheless, the illustration of several vertically and horizontally aligned nozzles should not be considered a limitation of the invention, as any other appropriate pattern may be used, including a fewer number of nozzles and nozzles of different sizes among each other. Also, the illustrated arms 9-10 which control the opening of said halves 20-21 can also be replaced by any other controlling device without departing from the purposed concept.

Figure 4:
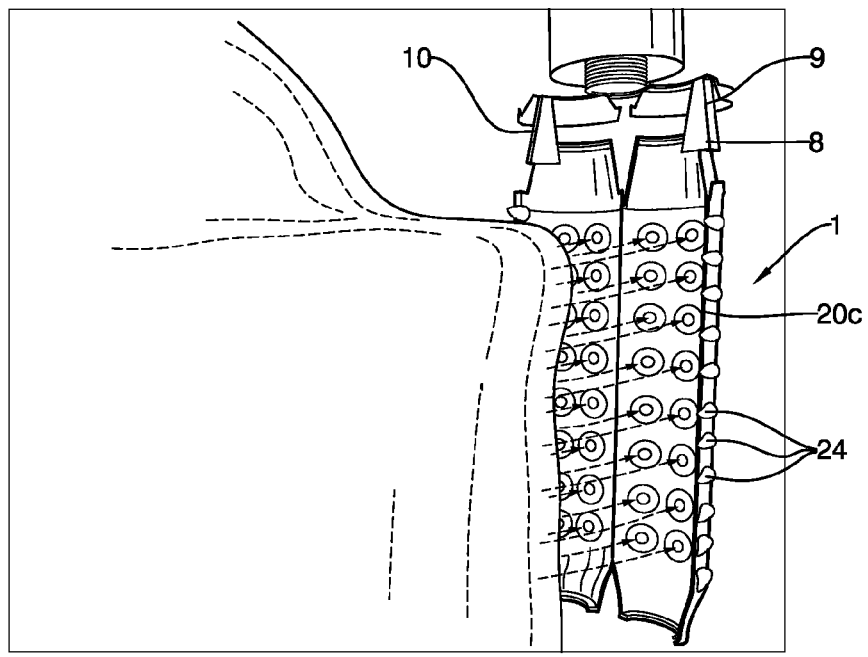
FIG. 4 is another perspective view showing that the suction effect has started and how the stomach walls go toward the suction nozzles as a response to said suction effect.

FIG. 4 illustrates the device open and the moment in which the surgeon connects and puts fluid communication in the vacuum device included in the endoscope (not illustrated) and the suction nozzles 24. This creates a strong suction effect (indicated with the arrows towards the nozzles in this Figure) that attracts the internal walls of the stomach to the device. As shown, the internal walls of the stomach approach the device and make physical contact with said nozzles 24. In this position, teeth 24 are inactive as well as the controlling device that are defined by the arms 9-10, which are in an 'on-hold' state.

Figure 5:
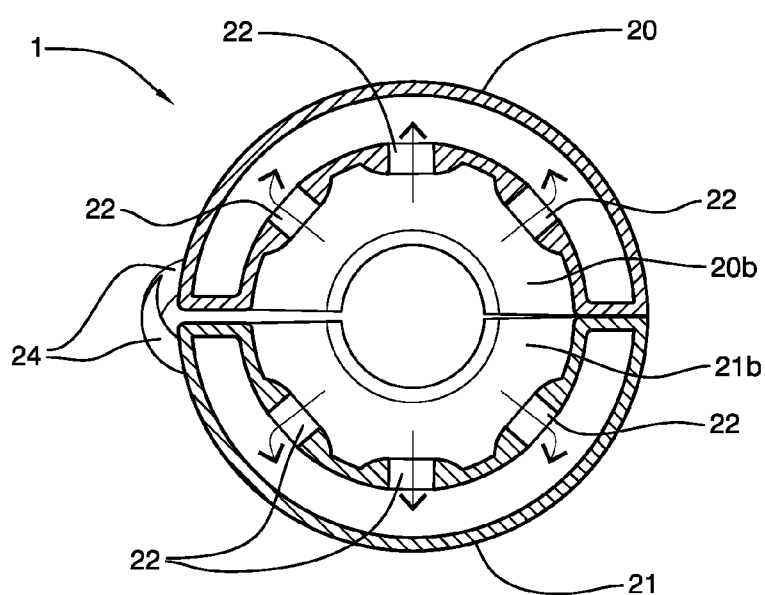
FIG. 5 is a cross sectional view of the apposition means showing the internal chamber in fluid communication with the nozzles.

FIG. 5 shows the device closed, holding part of the inner wall of the stomach 103. As a result of the above mentioned suction effect, a section of the internal wall of the stomach 103 reaches and takes contact with the inner walls of the device 1. In this moment, the surgeon operates on the controlling means 6 so as to close both halves 20-21 Said part of the stomach will remain inside the device 1 and the tips of teeth 24 will be stacked into the tissue, grabbing and keeping the tissue in place. It is important to point out that the material used to manufacture the inner walls of halves 20-21 is critical. The surgeon will leave the device in the illustrated closed position for a long time (several weeks or months) therefore the tissue of the stomach will be in permanent contact with this material. In order to avoid the necrosis of this tissue, the material used must be one of the several known materials in the market used to be in permanent contact with this tissue without creating problems for the patient.

Figure 6:
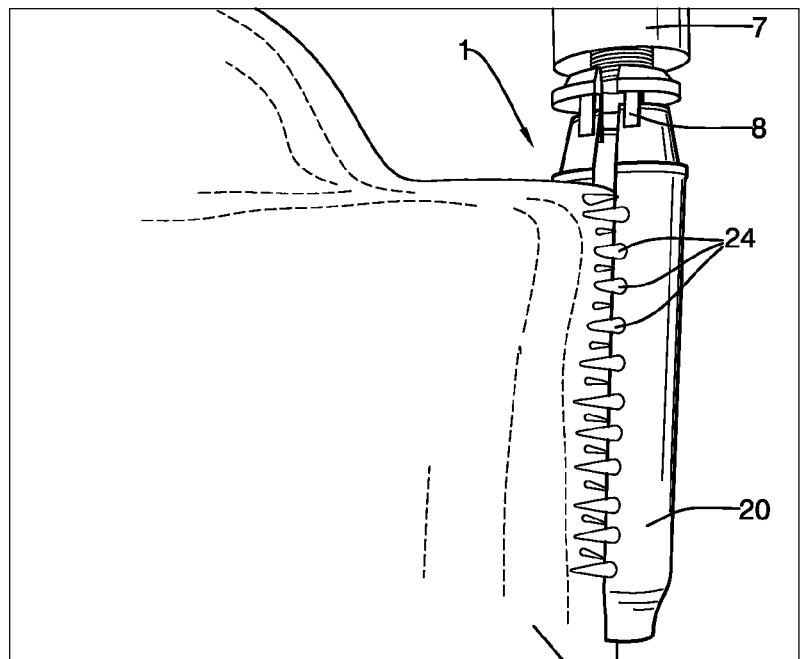
FIG. 6 is another perspective view showing how the stomach walls remain inside the device, the halves have been closed and the teeth and grabbing and keeping the tissue in place. The device is still attached to the elongated tube and the procedure is almost over; and finally.
Figure 7:
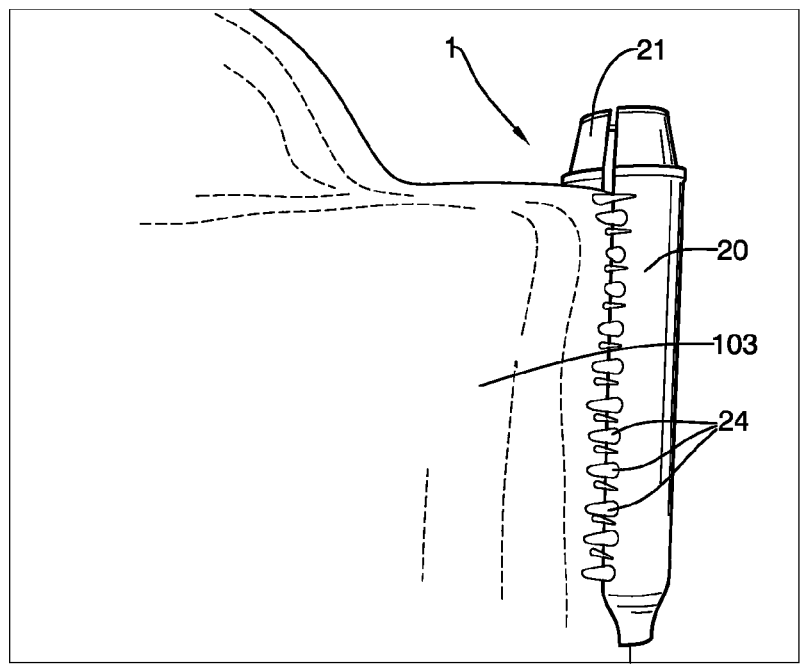
FIG. 7 is another perspective view this time that the device is no longer attached to the elongated tube. The surgeon has decoupled the distal end of the elongated tube from the device and taken the elongated tube out the patient's stomach and esophagus. The device will remain inside the stomach reducing the internal volume for the period of time the surgeon considers necessary to reduce the patient's weight.

FIG. 6 shows how the device will be left inside the stomach once the procedure is over. The surgeon will operate for the last time on the controlling means 6 to decouple the device from the head 7 of said elongated tube 2. Once the procedure is completed, the elongated tube 2 is withdrawn from the patient and the device 1 is left in the stomach. There are several alternatives for the surgeon to take the device out of the patient's body once the weight loss program reaches its goals. It may be manufactured out of biodegradable materials which allow the natural dissolution of the device in the gastric fluids. Another embodiment will involve using durable materials which will demand a new procedure. In such a case, the surgeon must insert the elongated tube again, couple the head 7 of the upper end of said device 1 to the distal end of the elongated tube, open the halves 20-21 for freeing the tissue of the stomach, then close the device again and take it out.

It is anticipated that the process will be an ambulatory process that is carried out using propofol intravenous anesthesiology, whereupon the patient can expect to consume liquids as soon as just few hours after the procedure is completed.

It is also possible to include, as part of the body of the purposed device, a safety feature to avoid problems for the patient in the case the device is disengaged from the stomach tissue after the procedure. Even though the design of the present device and the physical characteristics of the teeth used to grab the stomach tissue will make this possibility very remote, a disengagement between the device and the tissue may happen (for any reason). In such a case, there is a risk the device may fall into the antrum and then go to the pylorus, obstructing the stomach and putting the life of the patient in risk. To avoid this, the device may include, on its external body, several retention means defined by flexible rounded rings or legs that will prevent the device from entering into the pylorus in case a decoupling with the tissue happens. Said retention means will have the function of keeping the device away from the pylorus, having a diameter larger than the internal diameter of the pylorus.

The apposition of the stomach walls comprising the steps of:
a) navigating a distal end of an endoscopic apposition device to a treatment site, the apposition device having an elongated tube at the end of which the apposition means is attached, comprising a body with two hinged halves, each halve with a double wall that creates an internal chamber in fluid communication with a suction port of the elongated tube; the internal side of each halve has a plurality of suction nozzles in fluid communication with said chamber, and a set of grabbing teeth disposed on the outer edge of the device, and a hold and release mechanism;
b) advancing the device inside the stomach;
c) opening said halves exposing the suction nozzles to the inner walls of the stomach;
d) putting fluid communication in said nozzles with the vacuum means of the elongated tube;
e) applying vacuum to the internal chamber until the wall of the stomach is attached to the inner walls of said halves;
f) closing the device by punching the teeth to the stomach tissue, and securing the portion of tissue together;
g) detaching the endoscopic apposition device from the elongated tube; and
h) taking the device out of the patient's body.

When the present invention is used to create the apposition of other types of tissues, for example, a perforated stomach, a fistula, a hemorrhage, etc., the method for joining internal body tissue endoscopically comprises the steps of:
a) navigating a distal end of an endoscopic apposition device to a treatment site, the apposition device having a body with two hinged halves, each halve with a double wall that creates an internal chamber in fluid communication with a suction port of the elongated tube; the internal side of each halve has a plurality of suction nozzles in fluid communication with said chamber, and a set of grabbing teeth disposed on the outer edge of the device, and a hold and release mechanism;
b) advancing the device inside the body of the patient endoscopically;
c) opening said halves exposing the suction nozzles to the inner walls of the tissue to be joined;
d) putting fluid communication in said nozzles with the vacuum means of the elongated tube;
e) applying vacuum to the internal chamber until the tissue to be joined is attached to the inner walls of said halves;
f) closing the device by punching the teeth to the tissue, and securing the portion of tissue together;
g) detaching the endoscopic apposition device from the elongated tube; and
h) taking the device out of the patient's body.

While the preferred embodiments of the invention have been described above, it will be recognized and understood that various modifications can be made in the invention and the appended claims are intended to cover all such modifications which may fall within the spirit and scope of the invention.

I claim:

1. An implantable endoscopic apparatus for apposition of a wall of a stomach so as to reduce an internal volume of the stomach, the implantable endoscopic apparatus comprising:
an elongated endoscopic flexible tube having a proximal end and a distal end, said endoscopic tube having a vacuum channel formed therein;
a vacuum pump connected to said endoscopic tube so as to create a vacuum through said vacuum channel so as to create a vacuum at said distal end of said endoscopic tube;
a clamp-like body releasably affixed to said distal end of said flexible tube, said clamp-like body having a first half hingedly connected to a second half, each of said first and second halves having a first wall in spaced relation to a second wall so as to define an internal chamber in fluid communication with said vacuum channel of said endoscopic tube, said first wall having a plurality of suction nozzles in fluid communication with said internal chamber, said first half of said body having a first set of grabbing teeth formed along an edge thereof opposite the hinged connection with said second half, said second half having a second set of grabbing teeth formed along an edge thereof opposite the hinged connection with said first half; and
an actuator cooperative with said body so as to move said first and second halves between an open position and a closed position, said edges and said grabbing teeth of said first and second halves being spaced from each other in said open position, said edges of said first and second halves being adjacent each other in said closed position such that said first set of grabbing teeth intermesh with said second set of grabbing teeth.

2. The implantable endoscopic apparatus of claim 1, said body having an elongated cylindrical shape.

3. The implantable endoscopic apparatus of claim 1, said first set of grabbing teeth projecting outwardly of said edge of said first half, said second set of grabbing teeth projecting outwardly of said edge of said second half.

4. The implantable endoscopic apparatus of claim 1, each of the teeth of said first set of grabbing teeth being spaced respectively from each of adjacent teeth of said second set of grabbing teeth when said first and second halves are in the closed position.

5. The implantable endoscopic apparatus of claim 1, each of the teeth of said first and second sets of grabbing teeth being sharpened.

6. The implantable endoscopic apparatus of claim 1, said body being formed of a biodegradable material.

7. The implantable endoscopic apparatus of claim 1, said body being formed of a polymeric material.

* * * * *